United States Patent [19]

Passedouet et al.

[11] B 4,013,699
[45] Mar. 22, 1977

[54] ALUMINIUM AND/OR MAGNESIUM SALTS OF AMINO-ACIDS

[75] Inventors: André Henri Passedouet, Maisons-Laffite; Robert Pipon, Melle, both of France

[73] Assignee: Rhone-Poulenc S.A., Paris, France

[22] Filed: Aug. 8, 1974

[21] Appl. No.: 495,781

[44] Published under the second Trial Voluntary Protest Program on March 23, 1976 as document No. B 495,781.

[30] Foreign Application Priority Data

Aug. 9, 1973 France .............................. 73.29163
June 26, 1974 France .............................. 74.22228

[52] U.S. Cl. .................... 260/448 R; 260/534 R; 260/534 L; 424/317
[51] Int. Cl.² ............................................ C07F 5/06
[58] Field of Search ........ 260/448 R, 534 L, 534 R

[56] References Cited

UNITED STATES PATENTS

| | | | |
|---|---|---|---|
| 2,480,743 | 8/1949 | Krantz et al. | 260/448 R |
| 2,588,090 | 3/1952 | Delmar | 260/448 R |
| 2,907,781 | 10/1959 | Hermelin | 260/448 R |
| 3,450,752 | 6/1969 | Inklaar | 260/448 R X |
| 3,534,094 | 10/1970 | Koenig et al. | 260/534 |
| 3,651,137 | 3/1972 | Yee et al. | 260/534 L |
| 3,787,466 | 1/1974 | Kagawa et al. | 260/448 R |
| 3,809,760 | 5/1974 | Thely | 260/534 R |
| 3,836,551 | 9/1974 | Schroeder et al. | 260/448 R X |

OTHER PUBLICATIONS

Chemical Abstracts, V. 76, 60071c (1972).
Chemical Abstracts, V. 65, 17233f (1966).
Chemical Abstracts, V. 77, 168641y (1972).

Primary Examiner—Helen M. S. Sneed
Attorney, Agent, or Firm—Stevens, Davis, Miller & Mosher

[57] ABSTRACT

New salts of the formula:

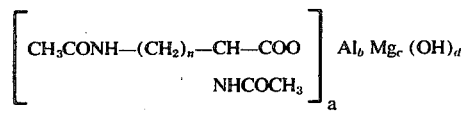

wherein $n$ represents 3 or 4, $a$ represents an integer from 1 through 10, $b$ represents zero or an integer from 1 through 9, $c$ represents zero or 1, at least one of the indices $b$ and $c$ representing an integer, and $d$ represents zero or an integer from 1 through 19, the numbers represented by the indices $a$, $b$, $c$ and $d$ being connected by the relationship $a + d = 3b + 2c$, possess pharmacological properties, and are particularly useful as anti-ulcer agents and as agents for protecting the gastrointestinal mucous membrane.

7 Claims, No Drawings

ALUMINIUM AND/OR MAGNESIUM SALTS OF AMINO-ACIDS

This invention relates to new therapeutically useful aluminium and/or magnesium salts, to a process for their preparation and to pharmaceutical compositions containing them The new metal salts of the present invention are those compounds of the general formula:

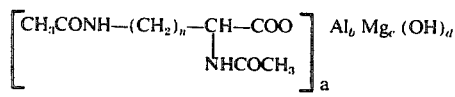

wherein the amino-acid moiety is of the D or L form or a mixture thereof, especially the DL form, $n$ represents 3 or 4, $a$ represents an integer from 1 to 10, $b$ represents zero or an integer from 1 to 9, $c$ represents zero or 1, at least one of the indices $b$ and $c$ representing an integer, and $d$ represents zero or an integer from 1 to 19, the numbers represented by the indices $a$, $b$, $c$ and $d$ being connected by the relationship $a + d = 3b + 2c$. When $b$ represents zero, preferably $d$ also represents zero, and when $c$ represents zero preferably $d$ is an integer from 1 to 19.

Preferred salts of the present invention are those of general formula I wherein:

$c$ represents zero, the indices $a$, $b$ and $d$ represent respectively 10, 9 and 17, or 5, 3 and 4, or 2, 7 and 19 when $n$ represents 3, and 6, 7 and 15 or 1, 1 and 2 when $n$ represents 4, $b$ represents zero, the indices $a$, $c$ and $d$ represent respectively 2, 1 and zero when $n$ represents 3, and $b$ represents an integer equal to or higher than 1 and $c$ represents 1, the indices $a$, $b$, $c$ and $d$ represent respectively 4, 2, 1 and 4 when $n$ represents 3 or 4.

According to a feature of the present invention, the salts of general formula I are prepared by the process which comprises (i) when $b$ represents zero and $c$ represents 1, reacting an aqueous solution of an amino-acid of the formula:

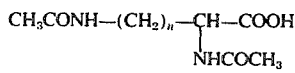

(wherein $n$ is 3 or 4), i.e. N,N'-diacetyl-ornithine or N,N'-diacetyl-lysine, with a reactive magnesium compound, or (ii) when $b$ represents an integer from 1 to 9 and $c$ represents zero, reacting an aqueous solution of an amino-acid of formula II with a reactive aluminium compound, or (iii) when $b$ represents an integer from 1 to 9 and $c$ represents 1, carrying out the reaction mentioned in (i) above and then reacting the resulting magnesium salt conforming to general formula I with a reactive aluminium compound, the amount of reactive magnesium compound and reactive aluminium compound employed in each reaction being such as to give the required number of gram atoms of magnesium and/or aluminium in the desired salt of general formula I.

In the preparation of magnesium salts and mixed magnesium aluminium salts of general formula I the reactive magnesium compound employed as reactant is preferably the oxide, hydroxide or an alkoxide. In its most preferred aspect, an aqueous suspension of magnesium hydroxide is reacted with the aqueous solution of the amino-acid of formula II at a temperature between 50° and 80°C.

In the preparation of aluminium salts and mixed magnesium aluminium salts of general formula I, the reactive aluminium compound employed as reactant is preferably an alkoxide, and more particularly an alkoxide obtained from an aliphatic alcohol containing 1 to 3 carbon atoms, such as aluminium methoxide, ethoxide or isopropoxide. In its most preferred aspect, a suspension of aluminium isopropoxide in isopropanol is reacted with an aqueous solution of the amino-acid of formula II, or with the magnesium salt resulting from the reaction of the reactive magnesium compound with an aqueous solution of the amino-acid of formula II, at a temperature between 50° and 80°C.

The salts of general formula I prepared according to the process of the present invention can be isolated from the reaction medium after concentrating the latter under reduced pressure and, where appropriate, treating the residue obtained with a poor solvent such as acetone.

The metal salts of general formula I possess useful pharmacological properties combined with low toxicity. They are particularly valuable as anti-ulcer agents and as agents for protecting the gastro-intestinal mucous membrane. They also possess good cicatrizant activity.

In animals the salts, used at doses of between 0.25 and 1g/kg animal body weight and administered orally, have proved active against gastric ulcers induced experimentally in rats in accordance with the technique of Shay H. et al., *Gastroenterology*, 5, 43 (1945), or in guinea-pigs, by the administration of histamine in accordance with the technique of Anderson W. and Watt J., *J. Physiol.* (London), 147, 52 p (1959).

The following Examples illustrate the preparation of the new metal salts of the invention.

EXAMPLE 1

Aluminium isopropoxide (183.6 g.; 0.9 mole) suspended in isopropanol (150 cc.) is added to N,N'-diacetyl ornithine (216 g.; 1 mole) dissolved in distilled water (900 cc.) at 60°C. After the end of the addition, the reaction mixture is stirred and heated at 60°C for 3 hours. The isopropanol is then removed by distillation under reduced pressure. After filtering the reaction mixture in order to remove the insoluble impurities, the clear and colourless filtrate is concentrated under reduced pressure so as to obtain a gel after removal of the water. The gel is taken up several times in acetone before a precipitate is obtained which can be filtered off. After drying the precipitate, an aluminium salt of N,N'-diacetyl-ornithine (254 g.) is obtained in the form of a white powder corresponding to the formula:

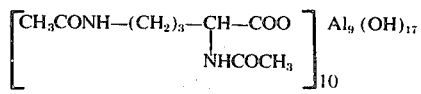

Al% = 8.7 (theory = 9.05)

EXAMPLE 2

Aluminium isopropoxide (147 g.; 0.72 mole) suspended in isopropanol (150 cc.) is added to N,N'-diacetyl-ornithine (259 g.; 1.2 moles) dissolved in distilled water (900 cc.) at 60°C. After the end of the addition, the reaction mixture is stirred and heated at 60°C for 3 hours. After treatment of the reaction mixture as in Example 1, an aluminium salt of N,N'-diacetyl-ornithine (250 g.) is obtained in the form of a white powder corresponding to the formula:

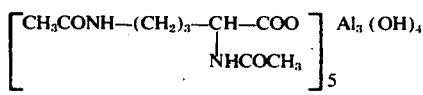

Al% = 6.8 (theory = 6.61)

EXAMPLE 3

Magnesium hydroxide (11.66 g.; 0.2 mole) suspended in water (20 cc.) is added to N,N'-diacetyl ornithine (172.8 g.; 0.8 mole) dissolved in distilled water (1,200 cc.) at 60°C. The reaction mixture is heated and stirred at 60°C for 30 minutes. Aluminium isopropoxide (81.6 g.; 0.4 mole) suspended in isopropanol (100 cc.) is added, and the mixture is then stirred and heated at 60°C for 30 minutes. After treatment of the reaction mixture as in Example 1, a mixed aluminium magnesium salt of N,N'-diacetyl-ornithine (175 g.) is obtained in the form of a white powder corresponding to the formula:

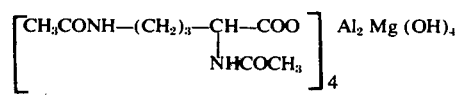

Al% = 5.45 (theory: 5.35) and Mg% = 2.36 (theory: 2.42).

EXAMPLE 4

Magnesium oxide (29.16 g.; 0.5 mole) suspended in water (100 cc.) is added to N,N'-diacetyl ornithine (216 g.; 1 mole) dissolved in distilled water (600 cc.) at 60°C. The mixture becomes clear after being stirred for 5 minutes at 60°C. Stirring is continued for a further 30 minutes at 60°C. After removing the water in a ventilated oven at 50°C, the residue is taken up in acetone (2 × 300 cc.), filtered off, drained and dried. The precipitate is taken up again in acetone (200 cc.) and then filtered off, drained and dried in a ventilated oven at 60°C.

The magnesium salt of N,N'-diacetyl-ornithine (190 g.) is thus obtained in the form of a white powder corresponding to the formula:

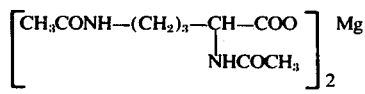

Mg% = 5.17 (theory = 5.34).

EXAMPLE 5

A solution of N,N'-diacetyl-L-ornithine (61.15 g.; 0.283 mole) in water (3.5 liters) is added, over the course of 15 minutes, with stirring and at a temperature of 50°-60°C. to a suspension of aluminium isopropoxide (202.4 g.; 0.992 mole) in isopropanol (300 cc.). After the end of the addition, the reaction mixture is stirred for 4 hours at 60°-65°C and then filtered. The filtrate obtained is concentrated to dryness under reduced pressure. The residue is washed several times with diethyl ether and then dried to constant weight under reduced pressure at 40°C. An aluminium salt of N,N'-diacetyl-L-ornithine (112.7 g.) is thus obtained in the form of a white powder corresponding to the formula:

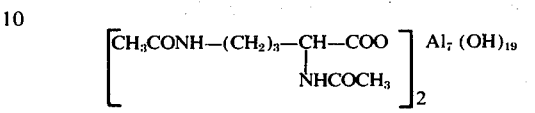

Al% = 19.8 (theory = 20.06%)

EXAMPLE 6

A suspension of aluminium isopropoxide (80.4 g.; 0.394 mole) in anhydrous isopropanol (80 cc.) is added, over the course of 15 minutes, with stirring and at 60°C. to a solution of N,N'-diacetyl-L-lysine (90.5 g.; 0.394 mole) in water (350 cc.). After the end of the addition, the reaction mixture is stirred for 3 hours at 60°C. The isopropanol is then removed by distillation under reduced pressure, the residue filtered and the filtrate concentrated to dryness under reduced pressure. The residue is washed with acetone, and the said product is filtered off and dried under reduced pressure. The aluminium salt of N,N'-diacetyl-L-lysine (102.6 g.) is thus obtained in the form of a white powder corresponding to the formula:

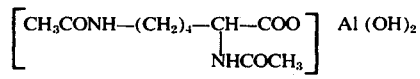

Al% = 9.25 (theory = 9.31)

EXAMPLE 7

Following the procedure of Example 6 but starting with N,N'-diacetyl-L-lysine (100 g.; 0.435 mole) dissolved in water (400 cc.) and with aluminium isopropoxide (103.5 g.; 0.507 mole) suspended in isopropanol (105 cc.), an aluminium salt of N,N'-diacetyl-L-lysine (118 g.) is obtained in the form of a white powder corresponding to the formula:

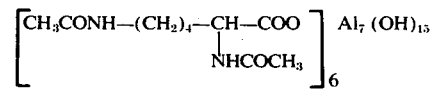

Al% = 10.5 (theory = 10.4%)

EXAMPLE 8

Magnesium hydroxide (3.5 g.) in water (6 cc.) is added to a solution, heated to 60°C, of N,N'-diacetyl-L-lysine (55.2 g.) and water (360 cc.), and then the reaction mixture is kept at 60°C for 30 minutes with stirring. A suspension of aluminium isopropoxide (24.5 g.) in isopropanol (30 cc.) is then added with stirring and while keeping the temperature at 60°C. The isopropanol is removed by distillation under reduced pressure (25 mm Hg). The reaction mixture is then filtered in order to remove insoluble material and the filtrate concentrated to dryness under reduced pressure (25 mm Hg) at 50°C. The paste-like residue obtained is triturated three times in acetone and then dried under reduced pressure (25 mm Hg). A solid is thus obtained which is washed by filtration using acetone (3 × 150 cc.). After drying, a mixed aluminium magnesium salt of N,N'-diacetyl-L-lysine (60.35 g.) corresponding to the formula:

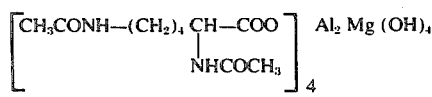

is obtained.

Analysis: Calculated% = C:45.18 H:6.83 N:10.54 Al:5.07 Mg:2.29. Found =C:44.8 H:6.9 N:9.95 Al:4.5 Mg:2.4.

The present invention includes within its scope pharmaceutical compositions comprising, as active ingredient, at least one of the salts of general formula I in association with a pharmaceutical carrier or coating. The invention includes especially such preparations made up for oral, parenteral or rectal administration or topical, especially dermal application, e.g. as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained.

The compositions according to the invention are particularly useful in human therapy in the treatment of gastrites and various gastralgias induced by other medicines, and in the treatment of ulcerous maladies (gastric or duodenal ulcers and peptic ulcers).

The compositions which contain one or more salts of general formula I in which the index c is 1 are useful in the treatment of disorders caused through magnesium deficiencies (neuromuscular disorders).

In human therapy, the dosages depend on the desired effect and on the duration of the treatment; they are generally between 1 and 5 g. per day when administered orally to an adult.

In general, the physician will decide the posology considered appropriate, taking into account the age, weight and other factors intrinsic to the patient being treated.

The following Examples illustrate pharmaceutical compositions according to the invention.

EXAMPLE 9

Tablets having the following composition are prepared in accordance with the usual technique:

| | |
|---|---|
| aluminium salt of N,N'-diacetyl-ornithine obtained as product in Example 1 | 0.500 g |
| starch | 0.150 g |
| precipitated silica | 0.095 g |
| magnesium stearate | 0.005 g |

EXAMPLE 10

Tablets having the following composition are prepared in accordance with the usual technique:

| | |
|---|---|
| aluminium salt of N,N'-diacetyl-lysine obtained as product in Example 7 | 0.500 g |
| starch | 0.150 g |
| precipitated silica | 0.095 g |
| magnesium stearate | 0.005 g |

We claim:

1. A salt of the formula:

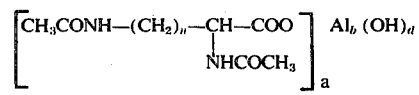

wherein the amino-acid moiety is of the D or L form or a mixture of the D and L forms, $n$ represents 3 or 4, $a$ represents an integer from 1 through 10, $b$ represents an integer from 1 through 9, and $d$ represents an integer from 1 through 19, the numbers represented by the indices $a$, $b$ and $d$ being connected by the relationship $a + d = 3b$.

2. A salt according to claim 1 wherein $n$ represents 3 and $a$, $b$, and $d$ represent 5, 3 and 4 respectively.

3. A salt according to claim 1 wherein $n$ represents 3.

4. A salt according to claim 1 wherein $n$ represents 3, and $a$, $b$ and $d$ represent 10, 9 and 17 respectively.

5. A salt according to claim 1 wherein $n$ represents 3, and $a$, $b$ and $d$ represent 2, 7 and 19 respectively.

6. A salt according to claim 1 wherein $n$ represents 4, and $a$, $b$ and $d$ represent 6, 7 and 15 respectively.

7. A salt according to claim 1 wherein $n$ represents 4, and $a$, $b$ and $d$ represent 1, 1 and 2 respectively.

* * * * *